US00PP13166P2

(12) United States Plant Patent
Doguet

(10) Patent No.: US PP13,166 P2
(45) Date of Patent: Nov. 5, 2002

(54) ZOYSIAGRASS PLANT NAMED 'ZEON'

(75) Inventor: David Doguet, Austin, TX (US)

(73) Assignee: Bladerunner Farms, Poteet, TX (US)

( * ) Notice: Subject to any disclaimer, the term of this patent is extended or adjusted under 35 U.S.C. 154(b) by 0 days.

(21) Appl. No.: 09/070,026

(22) Filed: Apr. 30, 1998

(51) Int. Cl.[7] ..... A01H 5/00
(52) U.S. Cl. ..... Plt./390
(58) Field of Search ..... Plt./390, 388

(56) References Cited

U.S. PATENT DOCUMENTS

PP9,127 P * 5/1995 Gibeault et al. ..... Plt./390
PP11,004 P 7/1999 Doguet ..... Plt./390
PP11,515 P 9/2000 Engelke ..... Plt./390
PP11,570 P 10/2000 Engelke ..... Plt./391

* cited by examiner

*Primary Examiner*—Bruce R. Campell
*Assistant Examiner*—W C Baker
(74) *Attorney, Agent, or Firm*—Streets & Steele; Jeffrey L. Streets

(57) ABSTRACT

This newly discovered asexually reproduced variety of zoysiagrass plant is a perennial having a superior rate of spreading with texture improved over common zoysiagrass, superior turf grass quality regarding compactness and low degree of thatch, and slightly darker than average green color.

2 Drawing Sheets

BACKGROUND OF THE INVENTION

The present invention relates to a new and distinct variety of a Zoysiagrass plant. The plant is a progeny that was discovered by David Doguet of Poteet, Tex., of a zoysiagrass plant in a collection of plants from Kobe, Japan made by Jack Murray (deceased). From these progenies, as seeds, were grown a collection of plants from which David Doguet discovered the single plant that was later cloned into sod and called 'Zeon'. Another zoysiagrass discovered by David Doguet, the variety 'JaMur', is the subject of the co-pending U.S. Patent Application, having Ser. No. 09/059,591.

For purposes of registration under the "International Convention for the Protection of New Varieties of Plants" (generally known by its French acronym as the UPOV Convention) and noting Section 1612 of the Manual of Patent Examination Procedures, the new variety of zoysia grass of the present invention is named 'Zeon'.

BRIEF SUMMARY OF THE INVENTION

The new zoysiagrass 'Zeon' possess high stolon frequency, good color, vertical posture, short stolon blade length, good perimeter stolon length, and short internode length. The blade length is about 6 cm long, having a width of about 4 mm. Mature plant height is from 6 to 12 cm.

DETAILED BOTANICAL DESCRIPTION

Figure 1:
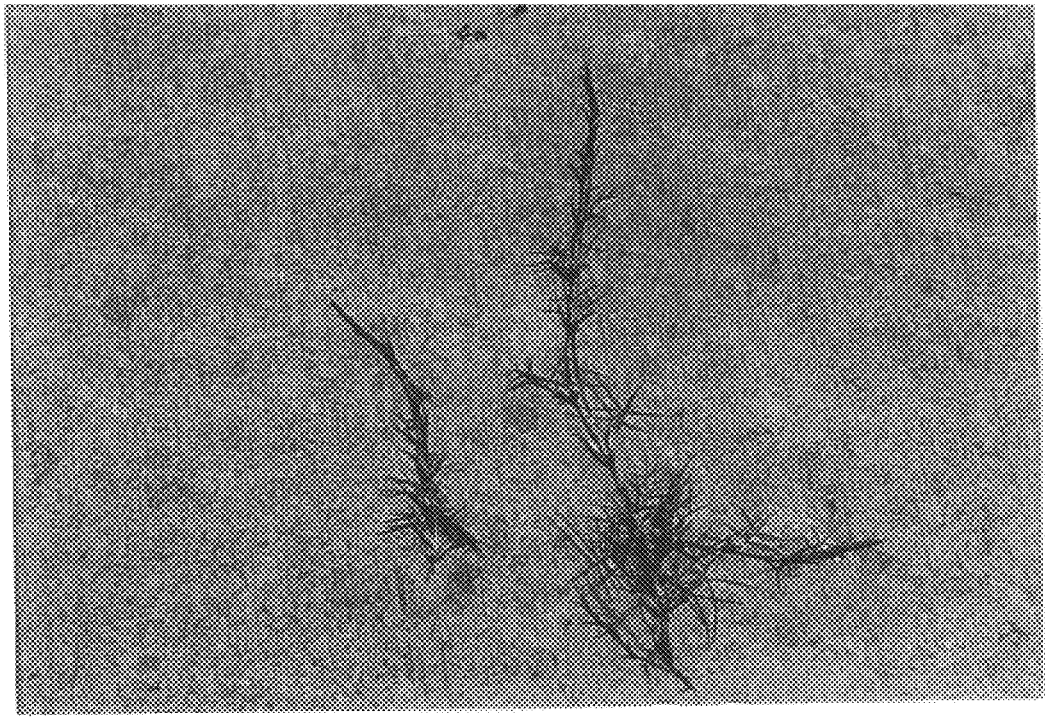
FIG. 1 is a photograph of an 'Emerald' plant on the left and a 'Zeon' plant on the right.
Figure 2:
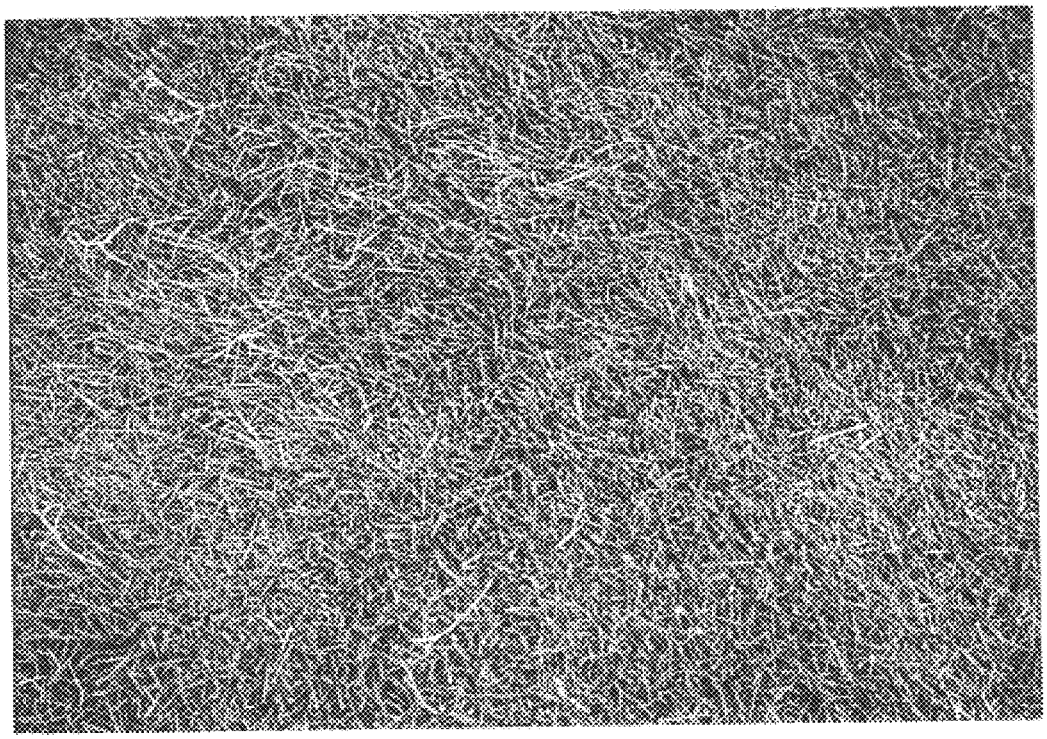
FIG. 2 is a photograph of 'Zeon' solid sod.
Figure 3:
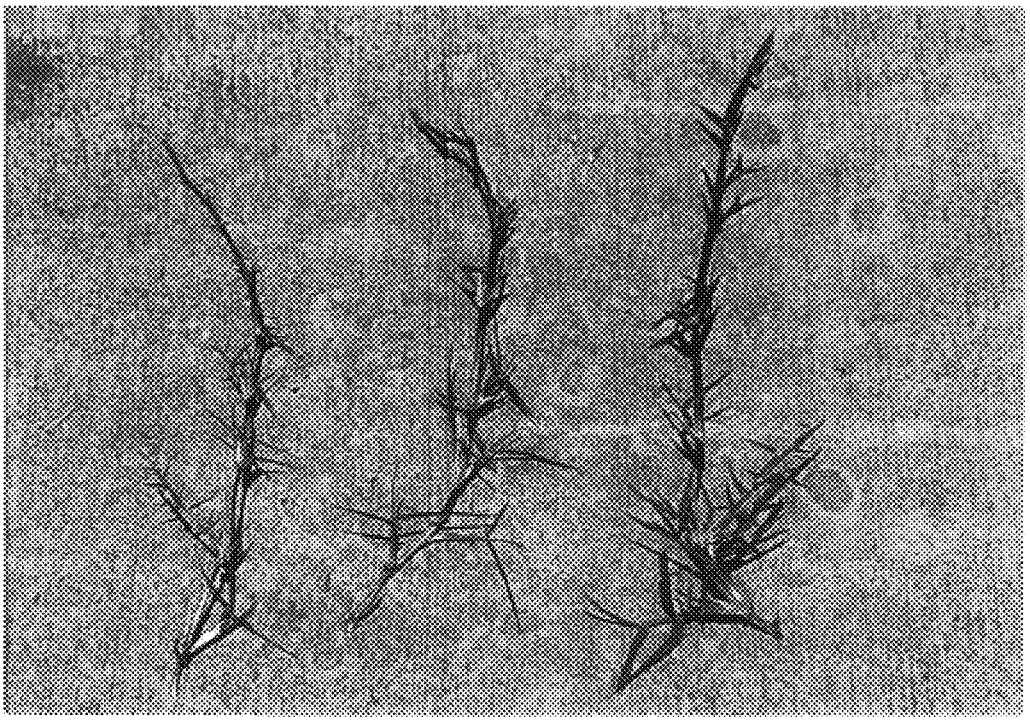
FIG. 3 is a photograph of three varieties of zoysiagrass plants with 'Zeon' on the left, 'Omni' center, and 'JaMur' on the right.
Figure 4:
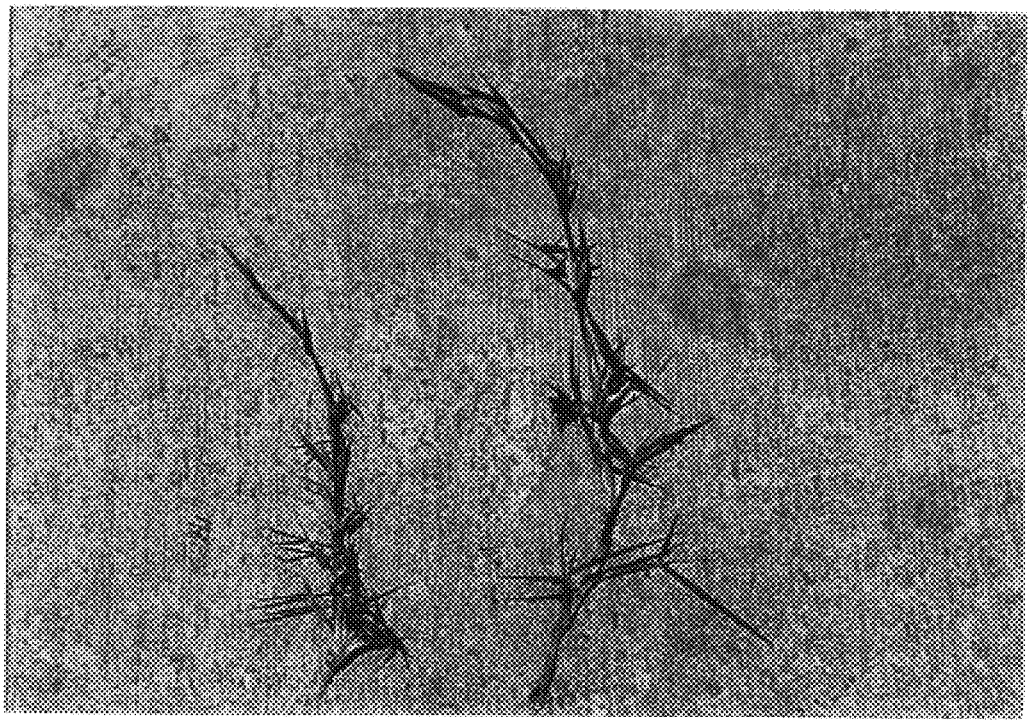
FIG. 4 is a photograph of two varieties of zoysiagrass plant with 'Zeon' on the left and 'Omni' on the right.

'Zeon' was characterized in greenhouse and field conditions and is a unique variety of zoysia grass developed as described above. 'Zeon' has been propagated by stolon cuttings in Poteet, Tex. and all traits of the plant have been found to be stable through successive generations of asexual propagation.

The grass was planted in 1996 and grown in Carbondale, Ill. as part of the National Zoysiagrass Test conducted by the National Turfgrass Evaluation Program (NTEP). 'Zeon' ranked higher in turf quality than 'Emerald' (unpatented) or 'Meyer' (unpatented) with color the same as 'Emerald' and 'Meyer', and, as seen in Table 1, has texture similar to that of 'Emerald' and finer than that of 'Meyer'. Further shown in Table 1, the thickness of thatch for 'Zeon' was less than all other cultivars shown other than for 'JaMur' and the posture of 'Zeon' is shown to be quite vertical.

TABLE 1

Traits of Selected Zoysiagrass Cultivars — Planted 1996, data 1997 and 2001, Carbondale, Illinois.

| | Stolon Length cm/m | Sod Spread cm | Stolon Freq. 9 = most | Texture 9 = finest |
|---|---|---|---|---|
| 'Chinese Common' | 127.1 | 2.7 | 7 | 2.0 |
| 'El Toro' | 311.6 | 4.9 | 9 | 4.3 |
| 'JaMur' | 426.5 | 4.7 | 9 | 5.7 |
| 'Meyer' | 48.6 | 2.2 | 5 | 7.3 |
| 'Emerald' | 91.2 | 1.3 | 5 | 8.3 |
| 'Zeon' | 372.0 | 1.2 | 5 | 9.0 |
| LSD 0.05 | 52.6 | 0.7 | | |

| | Thatch 9 = least | Posture 9 = vertical | Avg. Stolon Lgth cm |
|---|---|---|---|
| 'Chinese Common' | 2 | 6 | 14.66 |
| 'El Toro' | 4 | 8 | 17.38 |

TABLE 1-continued

Traits of Selected Zoysiagrass Cultivars — Planted 1996, data 1997 and 2001, Carbondale, Illinois.

| | | | |
|---|---|---|---|
| 'JaMur' | 9 | 4 | 17.42 |
| 'Meyer' | 3 | 9 | 5.55 |
| 'Emerald' | 1 | 7 | 6.56 |
| 'Zeon' | 8 | 8 | 11.60 |
| LSD 0.05 | | | 4.92 |

Comparisons are shown in Tables 2 through 4 of internode length, thickness, and color, number of nodes from stolon tip to first branch, rate of branching per stolon node, stolon blade length and width, stolon sheath length, shoot blade length and width, shoot sheath length, and blade and ligule hair length and frequency. Using this information, Zeon can easily be distinguished from the other varieties shown.

As shown in Table 2, the shoot blade length and sheath lengths of 'Zeon' were shorter than that of 'Meyer', but similar to that of 'Emerald'. The stolon blade width of 'Zeon' was greater than that of 'Emerald', but less than that of 'Meyer'. Its stolon sheath length was greater than those of 'Emerald' and 'Meyer' but shorter than those of 'El Toro' (U.S. Plant Pat. No. 5,845) and 'Chinese Common' (unpatented). The shoot blade widh of 'Zeon' was thinner than than for all the other varieties shown.

TABLE 2

Traits of Selected Zoysiagrass Cultivars — Planted 1996, data 1997 and 2001 Carbondale, Illinois.

| | Shoot Blade Length cm | Stolon Blade Length cm | Shoot Blade Width mm | Stolon Blade Width mm | Shoot Sheath Length cm | Stolon Sheath Length cm |
|---|---|---|---|---|---|---|
| 'Chinese Common' | 9.00 | 2.69 | 3.83 | 4.1 | 3.65 | 1.08 |
| 'El Toro' | 7.82 | 2.85 | 3.33 | 3.9 | 3.70 | 1.08 |
| 'JaMur' | 7.03 | 2.43 | 4.12 | 4.0 | 2.75 | 1.00 |
| 'Meyer' | 8.58 | 1.84 | 3.00 | 2.9 | 3.15 | 0.55 |
| 'Emerald' | 6.00 | 0.48 | 3.17 | 1.2 | 2.17 | 0.62 |
| 'Zeon' | 6.03 | 1.60 | 2.10 | 1.9 | 2.57 | 0.80 |
| LSD 0.05 | 0.94 | 0.31 | 0.50 | 0.4 | 0.49 | 0.16 |

As shown in Table 3, the blade hair length of 'Zeon' was less than that of 'Meyer' and the same as that of 'Emerald'. 'Zeon's' blade hairs were sparse, while those of 'Emerald' and 'Meyer' were frequent. Its ligule hairs were longer than those of 'Emerald' and 'Meyer'. The ligule hairs of 'Zeon' were dense, while those of 'Emerald' were absent and those of 'Meyer' were frequent. The internode color of 'Zeon' was red, like that of 'Meyer' while that of 'Emerald' was dark red. The internode length of 'Zeon' was greater than those of both 'Meyer' and 'Emerald' though the internode width of 'Zeon' was greater than that of 'Emerald' but less than that of 'Meyer'.

TABLE 3

Traits of Selected Zoysiagrass Cultivars — Planted 1996, data 1997 and 2001, Carbondale, Illinois.

| | Internode Length cm | Inter-node Width mm | Internode Color | Nodes to First Branch | Blade Hair Length mm | Ligule Hair Length mm |
|---|---|---|---|---|---|---|
| 'Chinese Common' | 4.65 | 2.00 | Dark Red | 4.00 | 2.8 | 2.00 |
| 'El Toro' | 4.13 | 1.00 | Dark Red | 1.67 | 1.2 | 2.17 |
| 'JaMur' | 4.78 | 1.95 | Dark Red | 2.00 | 1.0 | 1.95 |
| 'Meyer' | 1.82 | 1.88 | Red | 2.00 | 1.3 | 1.63 |
| 'Emerald' | 2.08 | 1.20 | Dark Red | 3.33 | 1.2 | 0.00 |
| 'Zeon' | 2.15 | 1.30 | Red | 1.50 | 1.0 | 2.50 |
| LSD 0.05 | 0.50 | 0.27 | | 0.61 | 0.3 | 0.30 |

As shown in Table 4, 'Zeon' had a perimeter stolon length greater than both 'Emerald' and 'Meyer'. The blade hair density was greater than all the other varieties shown except for 'Chinese Common'. 'Zeon' had fewer branches per node than either 'Emerald' or 'Meyer'.

TABLE 4

Traits of Selected Zoysiagrass Cultivars — Planted 1996, data 1997 and 2001, Carbondale, Illinois.

| | Blade Hair Density | Stolons per Meter | Leaf Surface with Rust | Hairs % | Perimeter Stolon Length cm | Branches per Node |
|---|---|---|---|---|---|---|
| 'Chinese Common' | 3.3 | 9.1 | 1.7 | 96 | 54.37 | 0.90 |
| 'El Toro' | 2.0 | 19.0 | 2.0 | 78 | 68.67 | 1.28 |
| 'JaMur' | 1.3 | 24.1 | 1.0 | 62 | 63.88 | 1.11 |
| 'Meyer' | 2.0 | 7.5 | 2.0 | 58 | 28.57 | 2.60 |
| 'Emerald' | 2.0 | 14.1 | 1.0 | 68 | 32.25 | 1.40 |
| 'Zeon' | 2.3 | 24.5 | 1.0 | 100 | 34.55 | 1.01 |
| LSD 0.05 | 0.7 | 5.5 | 0.9 | 29 | 9.44 | 1.04 |

Table 5 shows additional comparative data.

TABLE 5

Qualities of Turf in the National Zoysiagrass Cultivar Evaluation Trial, Planted 1996, Data 1997, Carbondale Illinois
Ratings- 9 = Darkest, Finest, Greatest, or Best

| | Turf Quality | | | | | | |
|---|---|---|---|---|---|---|---|
| | Color | Spg Grnp | Txtr | Jvn Vgr | May | Jun | Jul |
| HT-210 | 8.7 | 1.0 | 9.0 | 4.3 | 9.0 | 9.0 | 9.0 |
| DALZ 9601 | 8.0 | 7.7 | 9.0 | 4.0 | 8.7 | 8.7 | 8.7 |
| Zeon | 8.0 | 4.0 | 9.0 | 3.0 | 8.0 | 8.0 | 8.0 |
| FR | 8.3 | 1.0 | 9.0 | 1.0 | 7.7 | 7.7 | 7.7 |
| Emerald | 8.0 | 6.0 | 8.3 | 5.7 | 8.0 | 8.3 | 8.3 |
| DeAnza | 7.0 | 1.0 | 7.7 | 5.3 | 7.7 | 8.0 | 8.0 |
| Meyer | 8.7 | 9.0 | 7.3 | 7.7 | 7.7 | 8.0 | 8.3 |
| J-14 | 7.7 | 9.0 | 6.3 | 7.3 | 7.7 | 8.0 | 8.7 |
| Victoria | 8.3 | 2.3 | 7.0 | 5.3 | 6.7 | 7.0 | 7.0 |
| OH-1 | 7.0 | 3.7 | 9.0 | 3.7 | 5.3 | 6.0 | 6.0 |
| JaMur | 6.3 | 1.7 | 5.7 | 3.7 | 6.0 | 7.3 | 8.0 |
| 2040 | 8.3 | 1.0 | 5.7 | 1.0 | 6.0 | 6.0 | 6.0 |
| El Toro | 5.3 | 2.3 | 4.3 | 7.7 | 6.0 | 7.0 | 7.7 |
| J-37 | 7.7 | 8.3 | 5.0 | 8.3 | 5.3 | 6.0 | 6.0 |
| Zenith | 7.7 | 8.3 | 6.0 | 6.0 | 5.0 | 5.3 | 5.0 |
| Miyako | 6.7 | 1.3 | 4.0 | 8.3 | 4.3 | 5.0 | 5.7 |
| SS | 7.3 | 1.0 | 5.3 | 1.0 | 4.3 | 5.0 | 5.0 |
| ZEN-400 | 5.7 | 9.0 | 4.3 | 4.3 | 5.0 | 5.0 | 5.3 |
| J-36 | 6.7 | 9.0 | 3.0 | 8.7 | 3.0 | 3.7 | 3.3 |

TABLE 5-continued

Qualities of Turf in the National Zoysiagrass Cultivar Evaluation Trial, Planted 1996, Data 1997, Carbondale Illinois
Ratings- 9 = Darkest, Finest, Greatest, or Best

| | | | | | | | |
|---|---|---|---|---|---|---|---|
| ZEN-500 | 6.0 | 8.0 | 3.3 | 3.0 | 3.3 | 3.3 | 3.3 |
| Chinese Common | 4.7 | 9.0 | 2.0 | 7.0 | 3.0 | 3.3 | 3.7 |
| Korean Common | 4.7 | 1.0 | 1.0 | 1.0 | 3.3 | 3.7 | 4.3 |
| LSD 0.5 | 0.8 | 1.1 | 1.1 | 0.7 | 1.3 | 1.1 | 1.2 |

| | Turf Quality | | | | | |
|---|---|---|---|---|---|---|
| | Aug | Sep | Oct | Avg | % Sum Cover | % WtrKl |
| HT-210 | 9.0 | 9.0 | 9.0 | 9.0 | 1.0 | 1.0 |
| DALZ 9601 | 9.0 | 9.0 | 9.0 | 8.83 | 2.0 | 3.3 |
| Zeon | 8.7 | 9.0 | 9.0 | 8.44 | 1.7 | 2.0 |
| FR | 8.3 | 9.0 | 9.0 | 8.22 | 1.0 | 1.0 |
| Emerald | 8.3 | 8.0 | 8.0 | 8.17 | 2.3 | 4.7 |
| DeAnza | 8.3 | 8.0 | 8.0 | 8.00 | 1.3 | 1.0 |
| Meyer | 8.3 | 7.3 | 7.3 | 7.83 | 3.0 | 8.7 |
| J-14 | 8.0 | 7.0 | 7.0 | 7.72 | 3.7 | 8.7 |
| Victoria | 7.0 | 6.7 | 6.7 | 6.83 | 1.0 | 1.7 |
| OH-1 | 6.7 | 8.0 | 9.0 | 6.83 | 1.0 | 1.3 |
| JaMur | 7.0 | 5.7 | 5.0 | 6.50 | 1.0 | 1.7 |
| 2040 | 6.7 | 7.0 | 7.0 | 6.44 | 1.0 | 1.0 |
| El Toro | 6.3 | 5.3 | 5.0 | 6.22 | 4.0 | 2.0 |
| J-37 | 6.3 | 6.0 | 6.3 | 6.00 | 6.0 | 9.0 |
| Zenith | 6.0 | 6.7 | 7.0 | 5.83 | 5.0 | 8.3 |
| Miyako | 5.3 | 5.3 | 5.0 | 5.11 | 2.3 | 1.3 |
| SS | 5.0 | 5.0 | 5.0 | 4.89 | 1.0 | 1.0 |
| ZEN-400 | 5.0 | 4.3 | 4.3 | 4.83 | 6.3 | 8.7 |
| J-36 | 3.7 | 4.3 | 4.0 | 3.67 | 4.3 | 8.3 |
| ZEN-500 | 3.0 | 3.3 | 3.7 | 3.33 | 3.0 | 5.3 |
| Chinese Common | 3.3 | 3.0 | 2.7 | 3.17 | 6.7 | 9.0 |
| Korean Common | 3.3 | 2.0 | 1.7 | 3.06 | 5.0 | 1.0 |
| LSD 0.5 | 1.2 | 1.3 | 1.5 | 0.94 | 0.9 | 0.8 |

WtrKl = Winter Kill
Spg Grnp = Spring Greenup
Sum = Summer
Jvn Vgr = Juvenile Vigor

Variety

Origin: Cultivar of a single superior progeny of a superior vegetative plant selected from a collection of plants from Kobe, Japan.

Classification: Botanic: *Zoysia japonica* Steud.

Chromosome number: n=20 (Diploid)

Form: Monocot Gramineae

Growth habit: A perennial plant with a stoloniferous growth habit that also produces rhizomes. This allows vegetative commercial propagation. It is able to spread under competitive conditions favorable for stolon production. It has a fibrous root system that can have a depth of 1 to 75 cm. It will produce a dense, finely textured turf with medium dark green color throughout a growing season with temperatures ranging from around 45 F. to over 105 F.

Establishment rate:

*Plugs*.—8–24 weeks with irrigation.

*Sod*.—1–2 weeks.

*Sprigs*.—>one year.

Regions of adaptation: North/South from Northern Arkansas to Mexico, and East/West between both USA coasts. The full extent of Zeon's geographical adaptation may be greater and will only be limited by winter survival in colder regions and adequate precipitation in drier regions.

Blade:

*Length*.—6 cm.

*Width*.—4 mm.

*Pubescence*.—Sparse across full adaxial surface.

Mature plant height: 6–12 cm.

Above canopy stolon production: None.

Internode length: 2.1 cm.

Internode width: 1.3 mm.

Stolon color: Red.

Leaf color: The leaf color is medium dark green. More specifically, the adaxial leaf surface, based on The R.H.S. Colour Chart, is 137 B green group and the abaxial leaf surface is 137 B green group.

Soil adaptation: Most soils with adequate drainage from sand to heavy clay loams and acid to alkaline pH.

Colors: Based on R.H.S. Colour Chart, the anthers are 4 C yellow group, the stigmas are 157 B green-white group, the culms are 137 B green group and the blade hairs are 137 A.

What is claimed is:

1. A new zoysiagrass plant, substantially as herein described and illustrated.

* * * * *